US00PP32223P2

(12) United States Plant Patent
Wood

(10) Patent No.: US PP32,223 P2
(45) Date of Patent: Sep. 22, 2020

(54) ***WEIGELA* PLANT NAMED 'SMWFDFPD'**

(50) Latin Name: *Weigela florida*
Varietal Denomination: SMWFDFPD

(71) Applicant: Spring Meadow Nursery, Inc., Grand Haven, MI (US)

(72) Inventor: Timothy D Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,605

(22) Filed: Nov. 5, 2019

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct cultivar of *Weigela* plant named 'SMWFDFPD' is disclosed, characterized by pink flowers and dark foliage. Plants are round in habit. The new variety is a *Weigela*, normally produced as an outdoor garden plant.

2 Drawing Sheets

Latin name of the genus and species: *Weigela florida*.
Variety denomination: 'SMWFDFPD'.

BACKGROUND OF THE INVENTION

The new *Weigela* cultivar is a product of open pollination conducted by the inventor, Timothy Wood, in Grand Haven, Mich. The objective of the breeding program was to produce new *Weigela* colors and habits. The open-pollination resulting in this new variety was made during the Summer 2012.

The seed parent is the variety *Weigela florida* 'Verweig', U.S. Plant Pat. No. 16,824. The new variety was identified as a potentially interesting selection in Summer 2015, at a commercial nursery in Grand Haven, Mich.

Asexual reproduction of the new cultivar 'SMWFDFPD' by softwood cuttings was first performed in Summer 2015, at a nursery in Grand Haven, Mich. Subsequent propagation has shown that the unique features of this cultivar are stable and reproduced true to type in 4 successive generations.

SUMMARY OF THE INVENTION

The cultivar 'SMWFDFPD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMWFDFPD' These characteristics in combination distinguish 'SMWFDFPD' as a new and distinct *Weigela* cultivar;

1. Dark foliage.
2. Round plant habit.
3. Pink flowers.

PARENT COMPARISON

Plants of the new cultivar 'SMWFDFPD' are similar to plants of the seed parent in most horticultural characteristics, however, plants of the new cultivar 'SMWFDFPD' differ in the following;

1. New cultivar has dark foliage, whereas the parent has light green foliage with cream margins.
2. The new variety has darker pink flowers than the parent.

COMMERCIAL COMPARISON

Plants of the new cultivar 'SMWFDFPD' can be compared to the commercial variety *Weigela* 'Bramwell', U.S. Plant Pat. No. 18,513. These varieties are similar in most horticultural characteristics, however 'SMWFDFPD' differs in the following;

1. New cultivar has a dome-shaped habit, whereas this comparator has a more spreading habit.

BRIEF DESCRIPTION OF THE PHOTOGRAPHS

Figure 1:
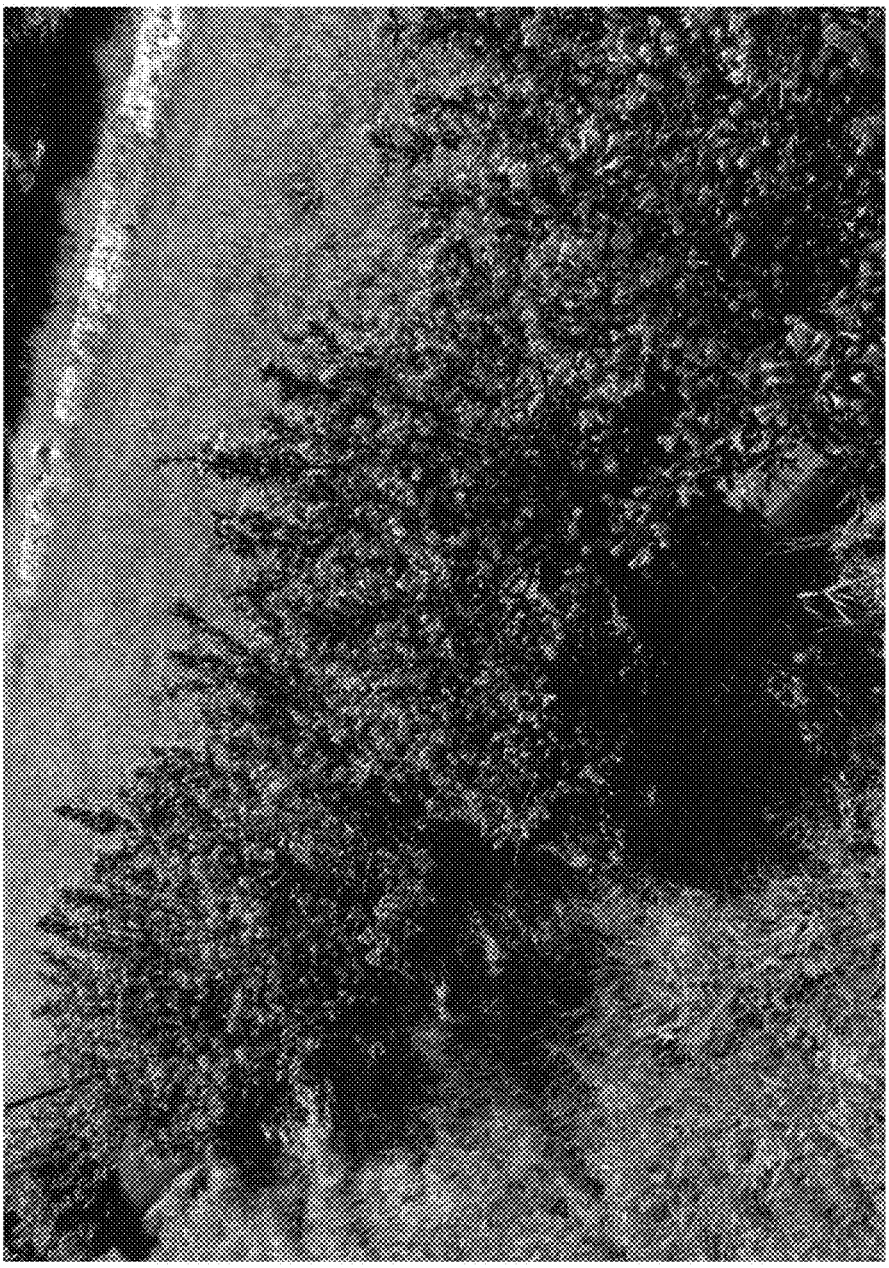

The accompanying photograph in FIG. 1 illustrates in full color typical plants of 'SMWFDFPD' in full bloom grown outdoors in a ground bed at about 2 years of age.

Figure 2:
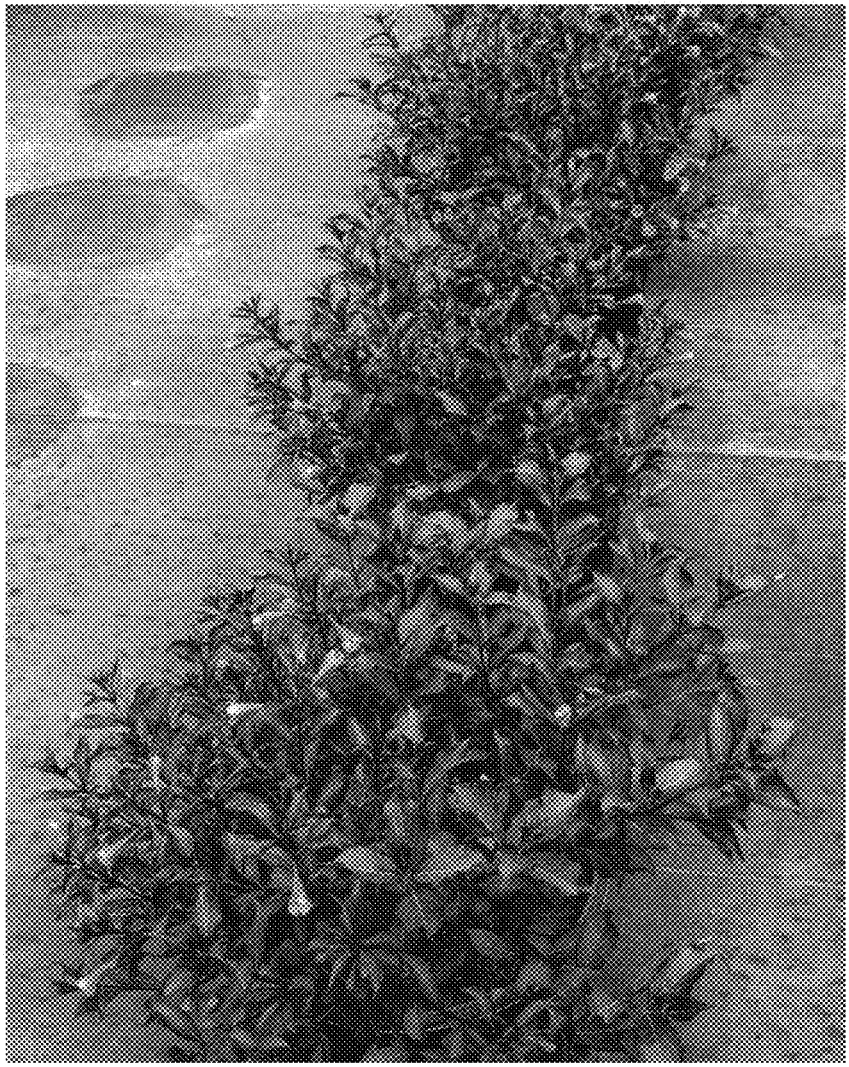

FIG. 2 illustrates typical plants grown in a 2 gallon pot, just beginning to flower at about 1 year of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMWFDFPD' plants grown in a polyhouse in Grand Haven, Mich. Measurements were taken during August 2017. The plants were 2 years old. The growing temperature ranged from approximately 5° C. to 27° C. Measurements and numerical values represent averages of typical plant types.

Botanical classification: *Weigela florida* 'SMWFDFPD'.

PROPAGATION

Time to initiate roots: Approximately 15 days.
Root description: Density is dense and freely branching. Thin and fibrous. White in color, not effectively measured with a color chart.
Time to produce a rooted young plant: Approximately 60 days.

PLANT

Plant type: Perennial shrub.
Age of plant described: Approximately 2 years old.
Growth habit: Upright and outward. Round.
Pot size of plant described: 3 gallon container.
Overall plant shape: Fairly compact and rounded.
Height: 76 cm.
Plant spread: 123 cm.
Growth rate: Good.
Plant vigor: Good.
Branching characteristics: Basal, very free branches.
Length of primary lateral branches: 62 cm.
Diameter of lateral branches: 5 mm.
Quantity of lateral branches: About 25.
Stem:
- *Stem characteristics*.—Rounded, two small ridges 180° apart on stem.
- *Stem strength*.—Strong.
- *Aspect*.—0 to 90°.
- *Color*.—RHS Brown 200C, bark Grey 201A.
- *Pubescence*.—Yes, predominantly on ridges.

Internode length: Average 2 to 4 cm.

FOLIAGE

Leaf:
- *Arrangement*.—Opposite.
- *Leaf shape*.—Ovate to oblanceolate.
- *Average length*.—Approximately 6-9 cm.
- *Average width*.—4 cm.
- *Apex*.—Acuminate.
- *Base*.—Cuneate.
- *Margin*.—Serrulate.
- *Texture of top surface*.—Leathery.
- *Texture of bottom surface*.—Leathery, with ridges for veins.
- *Pubescence*.—On underside midrib.
- *Color*.—Young foliage upper side: Near RHS Brown 200A. Young foliage under side: Near RHS Greyed-Purple N186C. Mature foliage upper side: RHS Green 144A with Greyed-Purple 183A. Mature foliage under side: RHS Yellow-Green 146C with some Greyed-Purple 183A.
- *Venation*.—Pattern: Pinnate. Color upper side: RHS Yellow-Green 151D. Color under side: RHS Yellow-Green 151D.
- *Petiole*.—Length: 8 mm. Diameter: 3.5 mm. Petiole color upper side: RHS Yellow-Green 144C with Greyed-Purple 185B on edges. Petiole color lower side: RHS Yellow-Green 144C. Petiole Texture: Some pubescence.
- *Other foliage characteristics*.—Dimensional, subtle fade between Purple and Red groups on foliage.

FLOWER

Natural flowering season: Summer.
Inflorescence type and habit: Umbel.
Inflorescence height: 10.5 cm.
Inflorescence width: 1.05 cm.
Quantity of flowers per inflorescence: 3 to 13.
Quantity of flowers and buds per plant: About 150.
Individual flowers:
- *Flower shape*.—Salverform.
- *Flower aspect*.—Mostly outward, some upward.
- *Flowering arrangement*.—Single salverform flower, majority grouped in 6-10.
- *Size*.—Diameter: 1.5 cm. Depth: 3 cm.
- *Persistence*.—Self-cleaning.
- *Fragrance*.—None.

Bud:
- *Shape*.—Obovate to spatulate.
- *Length*.—2 cm.
- *Diameter*.—5 mm.
- *Color*.—RHS Red-Purple 64A.

Petal:
- *Petal arrangement*.—Whorled, fused at opening of throat.
- *Number of petals per flower*.—5.
- *Petal shape*.—Rounded-obovate.
- *Petal base*.—Fused at throat.
- *Margin*.—Entire, slightly undulate.
- *Tip shape*.—Obtuse.
- *Length*.—7 mm.
- *Width*.—8.5 mm.
- *Texture*.—Upper: Soft, smooth, delicate. Lower: Soft, smooth, delicate.
- *Color*.—When opening: Upper side: Toward margin: RHS Red-Purple 70B. Further inside: Mix of RHS Red-Purple 67B and 62D. Under side: RHS Red-Purple 63A. Fully open: Upper side: RHS Red-Purple 64D. Under side: Mix of RHS Red-Purple 64A and D.
- *Flower tube*.—Length: 2 cm. Diameter, base: 2 mm. Color: RHS Red-Purple 64A.
- *Throat*.—Texture: Soft, smooth. Color: RHS Red-Purple 64D with a streak of Yellow 12B.

Sepal:
- *Arrangement*.—Unguiculate, fused at base.
- *Appearance*.—Long, narrowly triangular.
- *Number*.—5.
- *Shape*.—Narrowly triangular.
- *Tip*.—Acuminate.
- *Base*.—Obtuse.
- *Margin*.—Entire.
- *Length*.—6 cm.
- *Width*.—1 mm.
- *Texture, upper*.—Smooth, conaceous.
- *Texture, lower*.—Smooth, conaceous.
- *Color*.—Upper surface at maturity: RHS Greyed-Purple N186B. Under surface at maturity: RHS Greyed-Purple N186B.

Peduncle:
- *Length*.—2.2 cm.
- *Diameter*.—2 mm.
- *Color*.—RHS Greyed-Purple N186B.

*Orientation*.—0-80° from branch.
*Strength*.—Strong.
*Texture*.—Smooth.
Pedicel: None.

REPRODUCTIVE ORGANS

Stamens:
*Number*.—5.
*Filament length*.—1.3 cm.
*Filament color*.—RHS Red-Purple 67B.
Anthers:
*Shape*.—Linear, slightly oblong.
*Length*.—5 mm.
*Color*.—RHS Greyed-White 156B.
*Pollen color*.—RHS Greyed-White 156B.
*Pollen amount*.—Some.
Pistil:
*Number*.—1.
*Length*.—3.3 cm.
*Style*.—Length: 3.3 cm. Color: RHS Red-Purple 58A. Ovary Color: RHS Red-Purple 58A.
Stigma:
*Color*.—RHS Greyed-White 156B.
*Shape*.—Globular.

OTHER CHARACTERISTICS

Seeds and fruits: Not observed to set fruit and seeds.
Disease/pest resistance: Neither resistance nor susceptibility to normal diseases and pests of *Weigela* have been observed
Temperature tolerance: The new variety tolerates temperatures between −31° C. to 38° C.
Environmental stressors: Good tolerance to wind and rain.

What is claimed is:

1. A new and distinct cultivar of *Weigela florida* plant named 'SMWFDFPD' as herein illustrated and described.

* * * * *